(12) United States Patent
Schmidt

(10) Patent No.: US 7,745,794 B2
(45) Date of Patent: Jun. 29, 2010

(54) POSITRON EMISSION TOMOGRAPHY MODULE

(75) Inventor: Sebastian Schmidt, Weisendorf (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 12/149,208

(22) Filed: Apr. 29, 2008

(65) Prior Publication Data
US 2008/0283759 A1 Nov. 20, 2008

(30) Foreign Application Priority Data
Apr. 30, 2007 (DE) .................. 10 2007 020 363

(51) Int. Cl.
*G01T 1/164* (2006.01)
*A61B 5/05* (2006.01)

(52) U.S. Cl. .................. 250/363.03; 600/411

(58) Field of Classification Search ............ 250/363.02, 250/363.03, 363.04, 363.05, 363.08, 363.09, 250/370.09; 600/411
See application file for complete search history.

(56) References Cited

U.S. PATENT DOCUMENTS

| | | |
|---|---|---|
| 5,969,358 A | 10/1999 | DiFilippo et al. |
| 2004/0260171 A1* | 12/2004 | Graumann .................. 600/411 |
| 2006/0237652 A1* | 10/2006 | Kimchy et al. ......... 250/363.02 |
| 2006/0251312 A1 | 11/2006 | Krieg et al. |
| 2008/0001089 A1* | 1/2008 | Lusser .................. 250/363.02 |
| 2008/0208032 A1* | 8/2008 | Schuster et al. ............. 600/410 |
| 2008/0214927 A1* | 9/2008 | Cherry et al. ............... 600/411 |

FOREIGN PATENT DOCUMENTS

| | | |
|---|---|---|
| DE | 69732467 | 2/2006 |
| DE | 102005015070 | 10/2006 |

OTHER PUBLICATIONS

German Office Action corresponding to the German Priority Application 10 2007 020 363.4 dated Jan. 14, 2008.

* cited by examiner

*Primary Examiner*—David P Porta
*Assistant Examiner*—Faye Boosalis
(74) *Attorney, Agent, or Firm*—Harness, Dickey & Pierce, P.L.C.

(57) ABSTRACT

A positron emission tomography module is disclosed. In at least one embodiment, the positron emission tomography module includes a gamma ray detector arrangement designed such that it can alternately be combined with a magnetic resonance tomograph and with a computed tomograph.

12 Claims, 1 Drawing Sheet

POSITRON EMISSION TOMOGRAPHY MODULE

PRIORITY STATEMENT

The present application hereby claims priority under 35 U.S.C. §119 on German patent application number DE 10 2007 020 363.4 filed Apr. 30, 2007, the entire contents of which is hereby incorporated herein by reference.

FIELD

Embodiments of the present invention generally relate to a positron emission tomography module.

BACKGROUND

In addition to magnetic resonance tomography systems (MR scanners), computed tomographs (CT scanners), and positron emission tomography systems (PET scanners), combinations of positron emission tomography systems with computed tomographs or magnetic resonance tomography systems are also known.

For example, DE 10 2005 015 070 A1 describes a combined positron emission tomography and magnetic resonance tomography system, in which the positron emission tomography component is located in the examination space of the magnetic resonance tomography system.

DE 10 2006 054 542 likewise discloses a combined MR-PET system, in which the PET detector ring is arranged within the main magnet of an MR scanner but offset in the z-direction from the radio frequency coil of the MR scanner.

Furthermore, DE 697 32 467 T2 discloses a PET scanner, in which the gamma ray detectors can be rotated about the patient couch.

Both the combination of PET- and MR imaging and the combination of PET- and CT imaging have specific advantages. Hence, it would be desirable for both combined systems to be available. However, contrary to this wish, there are both high costs of a positron emission tomography system on the one hand, and the small number of examinations that can be carried out by it, and hence the low utilization, on the other hand.

In at least one embodiment of the invention, a possibility of allowing the requirement to be satisfied at a lower cost is created.

In at least one embodiment of the invention, a positron emission tomography module is designed such that it can alternately be combined both with a magnetic resonance tomograph and with a computed tomograph.

The positron emission tomography module of at least one embodiment includes at least one gamma ray detector arrangement. The additional electronics belonging to a PET scanner, such as the amplifier, analog-to-digital converter and power supply, can be integrated wholly or partly in the positron emission tomography module. However, the positron emission tomography module is preferably as slim as possible, so that it is portable and hence can be easily transported from one system to the other. The abovementioned additional electronic components are thus preferably accommodated in a carrying apparatus, explained in more detail below, or in the respective magnetic resonance tomograph or computed tomograph, which can be combined with the positron emission tomography module.

Combinability refers to, for example, that the positron emission tomography module can be placed both in or on a patient tunnel of a magnetic resonance tomograph and in or on a gantry of a computed tomograph. The patient tunnel of an MR scanner is the examination space into which the patient to be examined on a patient table is pushed. In the case of a conventional 1.5 T system with a superconducting main magnet this is a horizontally aligned tube in a cylindrical main magnet, the longitudinal axis of which defines the z-direction.

In embodiments of this application, the z-direction always refers to the movement direction of the patient table, which usually corresponds to the direction of the static main magnetic field in the aforementioned MR scanners. In the following, when referring to a computed tomograph, the z-direction likewise refers to the movement direction of the patient table, which usually corresponds to the axial direction of the tomograph.

The combinability of the positron emission tomography module with optionally an MR scanner or else a CT scanner means that the positron emission tomography module can be placed in or on the patient tunnel of an MR scanner or in or on the gantry of a CT scanner such that the patient on the patient table of the MR scanner or the CT scanner can be moved into the sensitive area of the gamma ray detector arrangement without having to be moved to another bed, or is already located in this sensitive area during the MR- or CT measurement. This can be achieved by inserting the positron emission tomography module directly into the patient tunnel of a magnetic resonance tomograph, or by placing it on these systems in a fashion offset in the z-direction from the patient tunnel of an MR scanner, or offset in the z-direction from the gantry of a CT scanner.

Even if the positron emission tomography module combined with an MR scanner or with a CT scanner is arranged slightly offset from the examination space of these scanners, the invention nevertheless allows a quasi-parallel acquisition of PET images and MR- or CT images. In the case of a given position of the patient within the combined arrangement of positron emission tomography module and MR- or CT scanner, an appropriate measurement can already be carried out in a first volume area of the patient in the examination area of the MR- or CT scanner, while PET signals are already being acquired simultaneously in a second volume area of the patient, located in the sensitive area of the gamma ray detector arrangement.

By subsequently pushing the patient on the patient table further through the arrangement, the first and the second volume can correspondingly be interchanged. Overall, the combined arrangement has a considerable speed advantage over back-to-back measurement of a patient in two separate systems. In particular, the patient does not have to be moved to another bed, so the PET images are directly comparable to the MR- or CT image data acquired in the examination space of the MR scanner or CT scanner.

During placement, it is preferable to prescribe a defined position with regard to the patient tunnel of the MR scanner, or to the gantry of the CT scanner, so that the images recorded by the respective imaging modalities can be related to one another spatially (registered) and hence can be directly compared with one another. For this purpose, the positron emission tomography module is preferably fixed to the MR scanner or the CT scanner using an interlocking connection, such as a latching- or snapping connection, or a clamping-, pressing-, screwed-, magnetic-, velcro- or adhesive connection. Preferably, both the magnetic resonance tomograph and the computed tomograph have appropriate recesses which allow an accurate fit when inserting corresponding bumps on the positron emission tomography module or a carrying apparatus belonging to it, which will be explained in more detail below.

The gamma ray detector arrangement includes, in at least one embodiment, an annular arrangement of gamma ray detectors, as is usual in the case of PET scanners. When placing the annular arrangement on the MR scanner or the CT scanner, it is preferably placed concentrically with the examination space of the respective scanner and, if appropriate, fixed to the scanner. The sensitive area of the gamma ray detector arrangement is thus preferably arranged offset in the z-direction from the respective examination space of the MR scanner or CT scanner. Preferably, the individual gamma ray detectors of the positron emission tomography module are screened from another by septa.

The weight of the arrangement of gamma ray detectors is preferably kept as low as possible so as to ensure easier portability of the positron emission tomography module. By way of example, the gamma ray detector arrangement can contain scintillation detectors or avalanche photodiodes, the latter being preferred since they can also be used within a strong main magnetic field of the MR scanner.

According to a first example embodiment, the positron emission tomography module is designed as a detachable positron emission insert for the patient tunnel of a magnetic resonance tomograph. Insert refers to the fact that the module can be inserted into the patient tunnel such that it is arranged concentrically with the examination space of the MR scanner. In this embodiment, the positron emission tomography module preferably comprises a detector ring made of gamma ray detectors which can be pushed into the patient tunnel. The same detector ring is preferably designed to be housed in an additional carrying apparatus of the computed tomograph. Such a carrying apparatus is preferably substantially in the form of an annulus or an annular segment and is fixed to the gantry in a fashion offset in the z-direction from the examination space of the computed tomograph. It is particularly preferred for the additional carrying apparatus to likewise be detachable from the computed tomograph, so that the gantry can be tilted without the positron emission insert.

In addition to the gamma ray detector arrangement, the positron emission insert preferably also comprises a part of the associated electronics, in particular an electronic unit for detecting and, if required, amplifying the detector signals generated by the gamma ray detectors.

Additional electronic modules, for example a power supply unit for the supply of current, and amplifiers, are preferably integrated in the carrying apparatus of the computed tomograph or in the MR scanner. Preferably, the signal leads and current supply lines are fed from the positron emission tomography module to the MR- or CT scanner or the carrying apparatus belonging to it via plug connectors. The plug connectors are preferably set up such that the electrical contacts are automatically made when the positron emission tomography module is placed or inserted into the magnetic resonance tomography, on the computed tomograph or into the carrying apparatus.

According to a second alternative embodiment, the positron emission tomography module has its own carrying apparatus, which can be assembled optionally next to the magnetic resonance tomograph or next to the computed tomograph. In this embodiment, the positron emission tomography unit is arranged offset in the z-direction from the patient tunnel of the MR scanner or the gantry of the CT scanner, respectively. As mentioned above, the carrying apparatus can contain components of the electronics, preferably a power supply unit for supplying the positron emission tomography module with energy and/or an evaluation unit for calculating image data from the detector signals.

By way of example, the carrying apparatus can be detachably fixed both to the gantry of the computed tomograph and to the housing of the MR scanner, for example by clamping, screwing, latching in, or inserting bolts or rails. Preferably, the carrying apparatus stands on the floor. Here it can either stand freely next to the MR- or CT scanner or it can be coupled to these scanners, in each case by way of a clamping-, snapping-, latching-, sliding- or other connection. In this case, this connection only serves to ensure a defined position of the carrying device with regard to the MR- or the CT scanner, so that the image data recorded with the respective modalities can be superposed on one another.

The carrying apparatus preferably has the shape of a tubular receptacle, with only a bottom segment of the tube being present, where appropriate, onto which the positron emission tomography module is placed.

It is particularly preferable for the carrying apparatus to be movably supported on rails so that it can be pushed directly to and fro between the MR- and the CT scanner.

In the two alternative embodiments, further electronic units and an EDP system for controlling the positron emission tomography module can be contained in both the MR- and the CT system. This has the advantage that only the actual detector module needs to be moved, whereas the control electronics for the PET are integrated into the MR- or CT scanner.

At least one embodiment of the invention also relates to a computed tomograph comprising a gantry which encloses an examination space and defines a z-direction along its axial direction. The computed tomograph has a carrying apparatus for an inventive positron emission tomography module, which is designed such that the longitudinal axis of the positron emission tomography module inserted into the carrying apparatus is aligned along the z-direction of the computed tomograph. Hence, the carrying apparatus keeps the positron emission tomography module offset from the examination space of the CT scanner in the z-direction. The positron emission tomography unit can be inserted into the carrying apparatus and can be taken out of it, so that it can also be inserted into another system, in particular an MR scanner. This achieves better utilization of the expensive positron emission tomography module.

Furthermore, at least one embodiment of the invention also relates to at a magnetic resonance tomograph which has a substantially tubular patient tunnel, which defines a z-direction along its axial direction. The magnetic resonance tomograph has a carrying apparatus, which is designed for detachably housing an inventive positron emission tomography module. The carrying apparatus is designed such that the longitudinal axis of the inserted positron emission tomography module is aligned along the z-direction of the magnetic resonance tomograph.

BRIEF DESCRIPTION OF THE DRAWINGS

In the following, advantageous example embodiments of the invention are described with reference to the figures.

DETAILED DESCRIPTION OF THE EXAMPLE EMBODIMENTS

Figure 2:
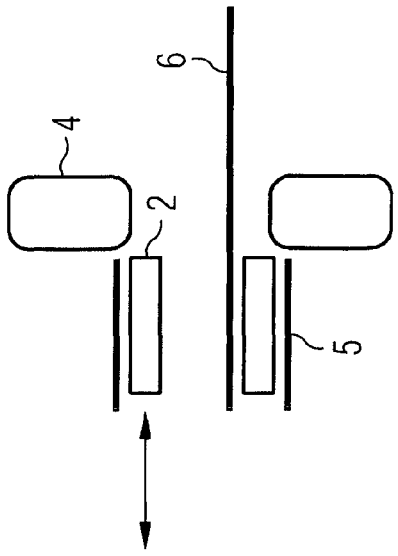
FIG. 2 shows the positron emission tomography module illustrated in FIG. 1 connected to a computed tomograph.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
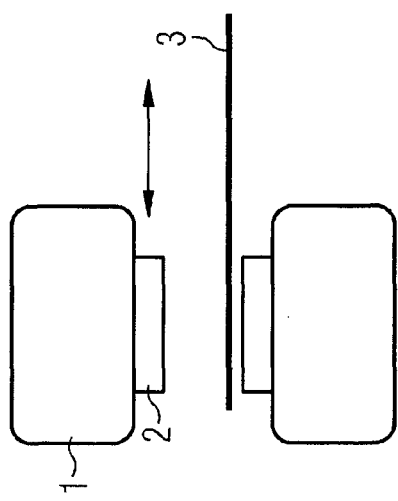
FIG. 1 shows a first example embodiment of a positron emission tomography module, designed according to the invention, combined with a magnetic resonance tomograph.

In the embodiment of the invention illustrated in FIGS. 1 and 2, the positron emission tomography module 2 is designed as an insert for the patient tunnel of the magnetic resonance tomograph 1 and is located within the latter's magnetic- and gradient system, while the patient to be examined is accommodated on the patient table 3. The positron emission tomography module 2 can be detached from the magnetic resonance tomograph 1 and can be connected to the computed tomograph 4, as shown in FIG. 2. For this purpose, the computed tomograph 4 is supplemented by a carrying structure 5, which can, for example, constitute a tubular receptacle.

Figure 4:
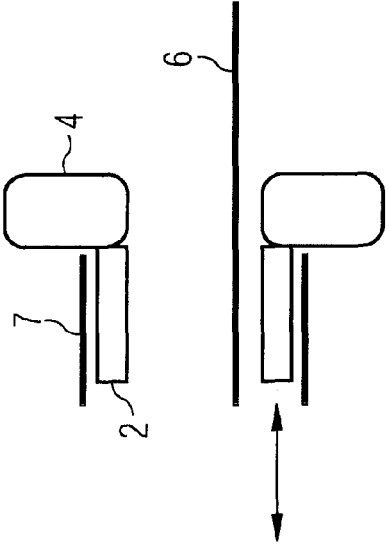
FIG. 4 shows the positron emission tomography module illustrated in FIG. 3 connected to a computed tomograph.
Figure 3:
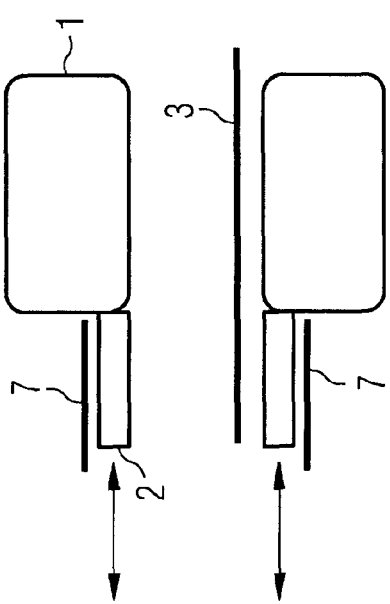
FIG. 3 shows a second example embodiment of a positron emission tomography module combined with a magnetic resonance tomograph.

FIGS. 3 and 4 show another example embodiment of the invention. In this case, the positron emission tomography unit 2 is arranged offset in the z-direction from the magnetic resonance tomograph 1. It has its own carrying structure 7, which can, together with the positron emission tomography module 2, be detached from the magnetic resonance tomograph 1 and can, as shown in FIG. 4, be connected to the computed tomograph 4. This dedicated carrying structure 7 also advantageously provides that the gantry can be tilted without the positron emission tomography module 2. In this case, the carrying structure 7 stands freely on the floor next to the computed tomograph 4 or the magnetic resonance tomograph 1; however, if applicable, it is connected to these by electric lines and preferably fixed to the MR scanner or CT scanner by a detachable connection.

The displacement of the carrying structure 7 between the computed tomograph 4 and the magnetic resonance tomograph 1 can be further eased by arranging it on rails.

At least one embodiment of the invention allows better utilization of the expensive positron emission tomography module 2. Further savings can be achieved since moreover, both the magnetic resonance tomograph 1 and the computed tomograph 4 can contain components, such as cooling apparatus, EDP system and further electronics, for example analog-to-digital converters, which can also be used by the positron emission tomography module 2.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A positron emission tomography module, comprising: a gamma ray detector arrangement, wherein the module is combinable both with a magnetic resonance tomograph and with a computed tomograph, wherein the module is designed as a detachable positron emission insert which can be inserted into the patient tunnel of a magnetic resonance tomography such that it is arranged concentrically with the examination space of the magnetic resonance tomography, and wherein the module is designed to be housed in an additional carrying apparatus of the computer tomograph, the carrying apparatus being in the form of an annulus or annular segment and being fixed to a gantry of the computed tomograph in a fashion offset in an axial direction from an examination space of the computed tomograph.

2. The positron emission tomography module as claimed in claim 1, further comprising an annular arrangement of gamma ray detectors.

3. The positron emission tomography module as claimed in claim 1, further comprising:
    an electronic unit for at least one of detecting and amplifying the detector signals generated by the gamma ray detector arrangement.

4. The positron emission tomography module as claimed in claim 1, wherein the carrying apparatus includes at least one of a power supply unit for supplying the positron emission tomography module with energy and an evaluation unit for calculating image data from the detector signals.

5. A computed tomograph, comprising:
    a gantry to enclose an examination space and define a z-direction along its axial direction; and
    a carrying apparatus of a positron emission tomography module as claimed in claim 1, wherein the carrying apparatus is designed such that a longitudinal axis of the inserted positron emission tomography module is aligned along the z-direction of the computed tomograph.

6. The computed tomograph of claim 5, wherein the carrying apparatus is in the form of an annulus or annular segment.

7. The computed tomograph of claim 5, wherein the carrying apparatus is detachably fixed to the gantry of the computed tomograph.

8. The computed tomograph as claimed in claim 5, wherein the carrying apparatus of the computed tomograph includes at least one of a power supply unit for supplying the positron emission tomography module with energy and an evaluation unit for calculating image data from the detector signals.

9. A magnetic resonance tomograph, comprising:
    a substantially tube-shaped patient tunnel which defines a z-direction along its axial direction; and
    a carrying apparatus of a positron emission tomography module as claimed in claim 1, wherein a longitudinal axis of the inserted positron emission tomography module is aligned along the z-direction of the magnetic resonance tomograph.

10. The magnetic resonance tomograph as claimed in claim 9, wherein the magnetic resonance tomograph includes at least one of a power supply unit for supplying the positron emission tomography module with energy and an evaluation unit for calculating image data from the detector signals.

11. The positron emission tomography module as claimed in claim 1, wherein the positron emission insert is designed to be housed in a carrying apparatus of the computed tomography in the form an annulus or annular segment.

12. The positron emission tomography module as claimed in claim 1, wherein the positron emission tomography module includes plug connectors for connecting signal leads and current supply lines to matching plug connectors in the magnetic resonance tomography or the computed tomograph when the positron emission tomography module is inserted into the magnetic resonance tomograph or into the carrying apparatus of the computed tomograph.

* * * * *